(12) United States Patent
Boström (10) Patent No.: US 9,656,026 B2
(45) Date of Patent: May 23, 2017

(54) NEEDLE SHEATH REMOVER ASSEMBLY (75) Inventor: Anders Boström, Solna (SE)

(73) Assignee: SHL Group AB, Nacka Strand (SE)

( * ) Notice: Subject to any disclaimer, the term of this patent is extended or adjusted under 35 U.S.C. 154(b) by 355 days.

(21) Appl. No.: 14/343,853

(22) PCT Filed: Jun. 15, 2012

(86) PCT No.: PCT/SE2012/050655
§ 371 (c)(1),
(2), (4) Date: Mar. 9, 2014

(87) PCT Pub. No.: WO2013/006119
PCT Pub. Date: Jan. 10, 2013

(65) Prior Publication Data
US 2014/0243753 A1 Aug. 28, 2014

Related U.S. Application Data (60) Provisional application No. 61/504,555, filed on Jul. 5, 2011.

(30) Foreign Application Priority Data

Jul. 5, 2011 (SE) ...................................... 1150630

(51) Int. Cl.
*A61M 5/32* (2006.01)
*A61M 5/20* (2006.01)

(52) U.S. Cl.
CPC ........ *A61M 5/3204* (2013.01); *A61M 5/3202* (2013.01); *A61M 5/3213* (2013.01);
(Continued)

(58) Field of Classification Search
CPC .............. A61M 5/3204; A61M 5/3213; A61M 2005/3215; A61M 2005/3217;
(Continued)

(56) References Cited

U.S. PATENT DOCUMENTS

| 5,024,666 A | * | 6/1991 | Pituch | A61M 5/3213 |
| | | | | 206/366 |
| 2006/0100588 A1 | * | 5/2006 | Brunnberg | A61M 5/3213 |
| | | | | 604/192 |
| 2010/0241087 A1 | * | 9/2010 | Moulton | A61M 25/0618 |
| | | | | 604/263 |

FOREIGN PATENT DOCUMENTS

WO 2006/009508 A1 1/2006
WO 2007/138296 A1 12/2007
(Continued)

OTHER PUBLICATIONS

EPO, Int'l Search Report in PCT/SE2012/050655, Aug. 10, 2012.
EPO, Written Opinion in PCT/SE2012/050655, Aug. 10, 2012.

*Primary Examiner* — Bhisma Mehta
*Assistant Examiner* — Brandy S Lee
(74) *Attorney, Agent, or Firm* — Piedmont Intellectual Property (57) ABSTRACT

The invention relates to a needle sheath remover comprising a cap (10) removably attached to a housing of a medicament delivery device, a sheath grabber (20) connected to said cap and configured to be engageable to a needle sheath (42) of a medicament container positioned (46) within said medicament delivery device, wherein the cap and the sheath grabber are axially movable in relation to each other and wherein the sheath grabber and the cap are configured to interact with each other such that upon removal of the cap from the housing, the sheath grabber is capable of engaging and removing said needle sheath.

13 Claims, 4 Drawing Sheets

(52) U.S. Cl.
CPC ......... *A61M 5/3219* (2013.01); *A61M 5/2033* (2013.01); *A61M 2005/3215* (2013.01)

(58) Field of Classification Search
CPC .............. A61M 5/3202; A61M 5/3205; A61M 5/3219; A61M 5/2033
See application file for complete search history.

(56) References Cited

FOREIGN PATENT DOCUMENTS

| | | |
|---|---|---|
| WO | 2009/081133 A1 | 7/2009 |
| WO | 2010/089589 A1 | 8/2010 |

\* cited by examiner

Fig. 4B

NEEDLE SHEATH REMOVER ASSEMBLY

TECHNICAL FIELD

The present invention relates to an assembly for the safe and easy removal of needle sheaths of medicament delivery devices.

BACKGROUND

Many medicament delivery devices on the market have been developed for self administration of medicament, where one large group is medicament injection devices. Many of these injection devices have been provided with removable needle cover assemblies where the core cover is a needle sheath.

These sheaths are arranged to protect an injection needle before use in order to keep the needle sterile and also to protect the user from unintentional needle sticks. The sheaths are pushed onto the neck portion of a medicament container, such as a syringe or cartridge, during assembly of container, needle and sheath. The sheath is preferably of a resilient material, normally rubber, which ensures a tight grip and a good seal between the outer environment and the syringe. However this tight grip also means that it is relatively difficult to remove the sheath from the syringe in order to perform an injection.

Therefore a number of sheath removal devices have been developed, which are intended to aid the user in removing the sheath. Documents WO2010089589 and EP2021057 disclose different solutions to this problem.

WO2010089589 describes a device in which a housing of an autoinjector comprises an axially extending boss positioned to interfere with cam surfaces of axially extending fingers of a needle sheath removing means. During axial separation, the interference of the cam surfaces and the boss forces the fingers to flex radially inwards to grip a needle sheath of the autoinjector. This solution suffers the disadvantage of having the boss integrated with the housing, i.e. stationary, as the needle sheath moves axially in relation to the housing. If the fingers do not attain a good grip until the cam surfaces fully enter the narrow passage formed by the boss of the housing, the sheath may refuse to move and the fingers will slide. The sheath remover also risks getting stuck due to tolerance mismatch which may cause passage of the boss/housing to be too narrow for the cam surfaces to be able to enter it. Also, the proposed design of the autoinjector housing is very complicated to manufacture.

EP2021057 describes a cap for an injection device comprising a first part with a grip means for engaging the rear surface of a needle sheath at a neck portion of a medicament container. Upon assembly of the device the first part is attached to the front end of the injection device such that the grip means snap into engagement behind the needle sheath. A second part is subsequently attached to the first part to prevent the grip means from disengaging the rear surface of the sheath.

To grip behind the needle sheath is difficult since tolerances from assembling the containers and needle sheaths are not very accurate. If, during assembly of sheath, needle and container, the sheath is pushed far onto the neck portion of the container there may not be enough room for the fingers of the grip means to engage behind the sheath. Also, the grip is not very tight since it only depends on the grip means flexing radially behind the sheath and then being locked by the second part. There is no force to squeeze the sheath during removal. Therefore, such a solution would risk losing its grip on a soft rubber needle sheath.

An added disadvantage is that as the user tries to remove the cap and the sheath from the injection device he will have to overcome the friction between the cap and the device as well as the friction between the sheath and the needle at the same time. It may be difficult for users with weak hands, or for users with impaired manual dexterity, to overcome the accumulated force of the two friction interfaces.

Therefore, there is a need for a device that can securely remove a needle sheath from a needle regardless of the tolerances of the container or sheath. The device should also require little strength to remove and should be simple to manufacture.

SUMMARY

According to the main aspect of the invention, it relates to a needle sheath remover assembly for use in a medicament delivery device, axially elongated in a proximal and a distal direction, comprising a cap configured to be removably attached to a housing of a medicament delivery device, a sheath grabber connected to said cap and configured to be engageable to a needle sheath of a medicament container positioned within said medicament delivery device, wherein said cap and said sheath grabber are axially movable in relation to each other and wherein said sheath grabber and said cap are configured to interact with each other such that upon removal of said cap from the housing, said sheath grabber is capable of engaging and removing said needle sheath.

According to another aspect of the invention, said sheath grabber comprises second stop means and engaging means and wherein said cap comprises second blocking means and biasing means.

According to a further aspect of the invention, said cap is coaxially movable relative to the sheath grabber preferably wherein movement of the sheath grabber is restricted by the interaction between the biasing means and the engaging means such that the grabber is biased to engage the sheath and wherein movement of the cap relative to the sheath grabber is restricted by the interaction between the second blocking means and the second stop means such that the cap, the grabber and the sheath can be removed from the device According to yet another aspect of the invention the cap comprises an outer tubular member and an inner coaxial tubular member.

According to yet a further aspect of the invention, said outer tubular member and said inner tubular member are integrally arranged, or joined together, by a generally annular transversal wall, extending between the proximal ends of the inner and outer tubular members.

According to another aspect of the invention the sheath grabber is coaxially and slidably arranged within the inner tubular member of the cap.

According to a further aspect of the invention said sheath grabber further comprises first stop means, and wherein said cap further comprises guide means and first blocking means arranged to said guide means.

According to yet another aspect of the invention said first stop means is slidably arranged to said guide means and configured to interact with said first blocking means for holding the sheath grabber within the cap.

According to yet a further aspect of the invention said second stop means is a transversal member, wherein said engaging means comprises at least two radially resilient flexible arms extending longitudinally from said transversal member, and wherein said first stop means is a flexible latch member integral with, or attached to, the at least two radially resilient flexible arms.

According to another aspect of the invention each of the at least two radially resilient flexible arms comprises hooks or radially inwardly directed edges, grooves and/or protrusions for improving friction and/or connection between the engaging means and the needle sheath.

According to a further aspect of the invention said second blocking means is at least two longitudinally extending ribs on the inner circumferential surface of said inner tubular member.

According to yet another aspect of the invention the guide means is at least two longitudinally extending grooves or ridges on the inner circumferential surface of said inner tubular member and wherein the first blocking means is in the form of a distally directed surface or a ledge arranged inside or integrally within each of the at least two longitudinally extending grooves or ridges.

According to yet a further aspect of the invention the biasing means is configured as a number of radially protruding, longitudinally elongated fins equally spaced around the inner circumferential surface of the inner tubular member, wherein the fins are ramp-shaped, such that the sloping edges of the fins slope from the inner surface of the inner tubular member in a direction towards the distal end of said inner tubular member.

According to another aspect of the invention the fins protrude up to a predetermined height at a predetermined distance from the distal end of the inner tubular member, and wherein said height and distance are adapted to the configuration of the engaging means for biasing said engaging means radially inwards and thereby achieving a maximum engaging force between the engaging means and the needle sheath when the cap is coaxially movable relative to the sheath grabber.

According to a further aspect of the invention the second stop means is positioned at a predetermined distance from the second blocking means when the cap is attached to the device and wherein the second stop means and the second blocking means abut each other when the cap is coaxially moved in relation to the grabber said predetermined distance such that the cap biases the sheath grabber to move axially.

The present invention has a number of advantages. The ability of relative movement between the cap and the sheath remover allows the grip on the sheath to be increasingly tightened as a user pulls the cap from the housing, up to a point where the cap starts to pull the sheath remover, and consequently the sheath, from the needle, at which point the grip is at its strongest. The sheath remover assembly will continue to grip the sheath throughout the removal process - actually even after the sheath has been completely removed.

Thus, since the gripping member and the cap are linked to each other and the biasing member is also a part of the remover assembly the gripping force will remain strong throughout the process. The remover assembly also does not risk getting stuck at the housing due to tolerance mismatch.

In addition, as the user pulls at the cap, the cap will first come loose from the housing. Then the cap will engage the sheath remover and the sheath to remove the latter from the needle. Consequently, the removal of cap and needle sheath is divided into two steps such that the frictional force between the cap and the housing is overcome in the first step, followed by overcoming the frictional force between the sheath and the needle in the second step. Therefore the cap and the needle sheath are easy to remove, even for users with weak hands or with impaired manual dexterity.

Experiments have also shown that the sheath remover assembly is capable of removing a rigid needle shield (RNS) from a needle. A rigid needle shield is characterized in that the soft rubber sheath is surrounded by a rigid plastic or metal casing.

BRIEF DESCRIPTION OF THE DRAWINGS

In the following description of embodiments of the invention, reference will be made to the accompanying drawings of which.

DETAILED DESCRIPTION

Embodiments of the present invention will now be described in detail. As should be noted in the present application, when the term "distal part/end" is used, this refers to the part/end of the delivery device, or the parts/ends of the members thereof, which is/are located the furthest away from the medicament delivery site of the patient. Correspondingly, when the term "proximal part/end" is used, this refers to the part/end of the delivery device, or the parts/ends of the members thereof, which, is/are located closest to the medicament delivery site of the patient.

According to a main aspect of the invention it relates to a needle sheath remover assembly for use in a medicament delivery device, axially elongated in a proximal and a distal direction, comprising a cap configured to be removably attached to a housing of a medicament delivery device, a sheath grabber connected to said cap and configured to be engageable to a needle sheath of a medicament container positioned within said medicament delivery device, wherein said cap and said sheath grabber are axially movable in relation to each other and wherein said sheath grabber and said cap are configured to interact with each other such that upon removal of said cap from the housing, said sheath grabber is capable of engaging and removing said needle sheath.

Figure 1:
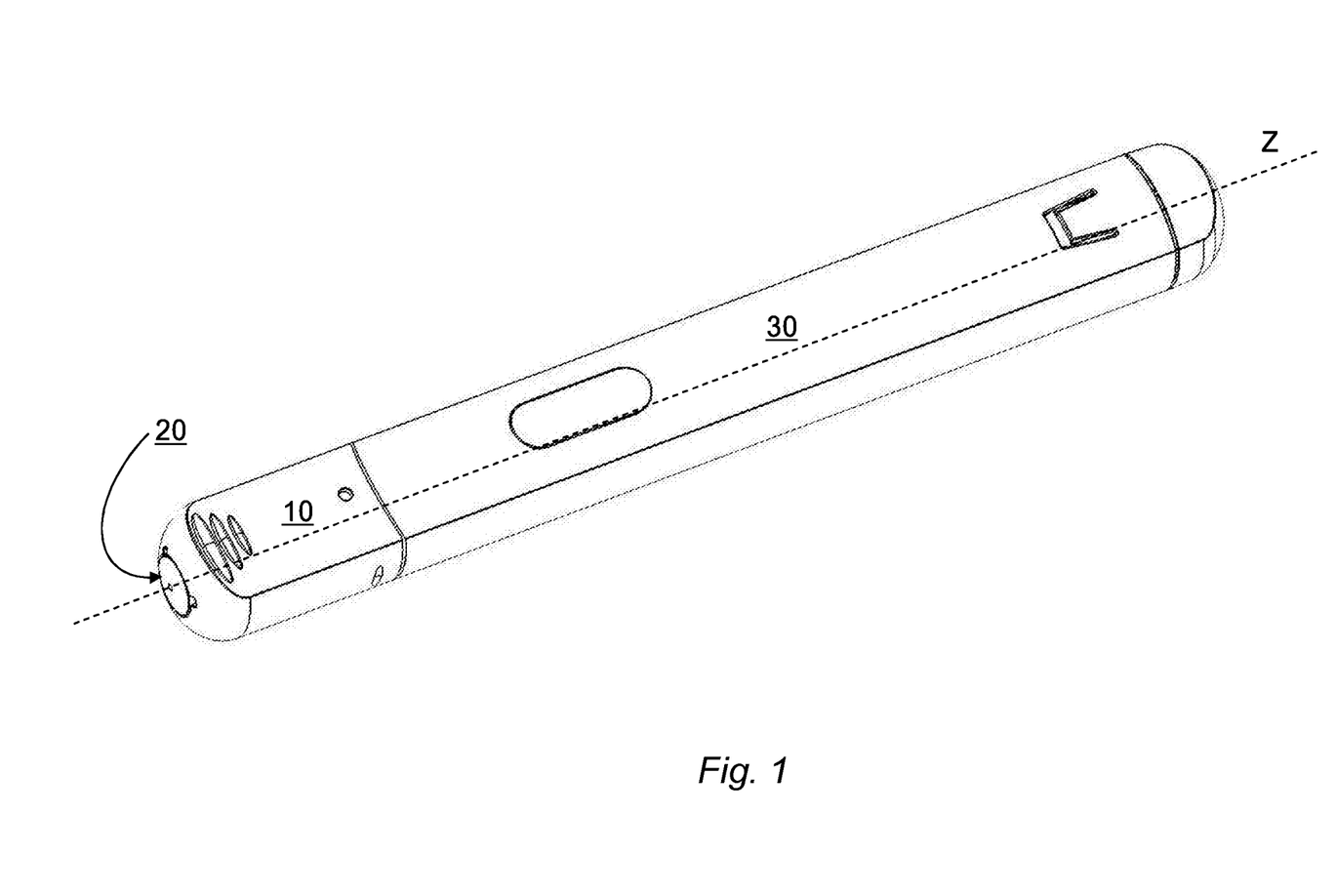
FIG. 1 is a perspective view of an exemplary embodiment of the present invention when assembled to a medicament delivery device.

An exemplary embodiment of the present invention is shown in the FIGS. 1-4. FIG. 1 is a perspective view of a medicament delivery device 30 which is elongated along a longitudinal axis Z and has a proximal end and a distal end. In the text below, references will be made to the longitudinal axis Z. Terms such as axial, axially, longitudinal, longitudinally, coaxial, along an axis or around an axis all refer to movements and/or positions in relation to the longitudinal axis Z.

Also, when referring to a radial inward or radial outward direction, it is taken to mean a direction orthogonally towards or orthogonally away from the longitudinal axis Z, respectively.

The exemplary delivery device of FIG. 1 is an auto injector, but could in practice be any kind of delivery device having a needle sheath that has to be removed prior to administration of its contents.

The figures show a soft needle sheath, e.g. rubber, but the sheath could also be a rigid needle shield (RNS), wherein a rigid casing, e.g. plastic or metal, fixedly surrounds a soft sheath.

The device shown in FIG. 1 comprises a housing 32 (FIG. 2) to which proximal end is attached a sheath remover assembly according to the present invention. The sheath remover assembly comprises a cap 10, removably attached to the housing, and a sheath grabber 20. The cap 10 and the sheath grabber 20 are mechanically connected but movable in relation to each other along the longitudinal axis Z within certain limits, as will be explained below.

Figure 2:
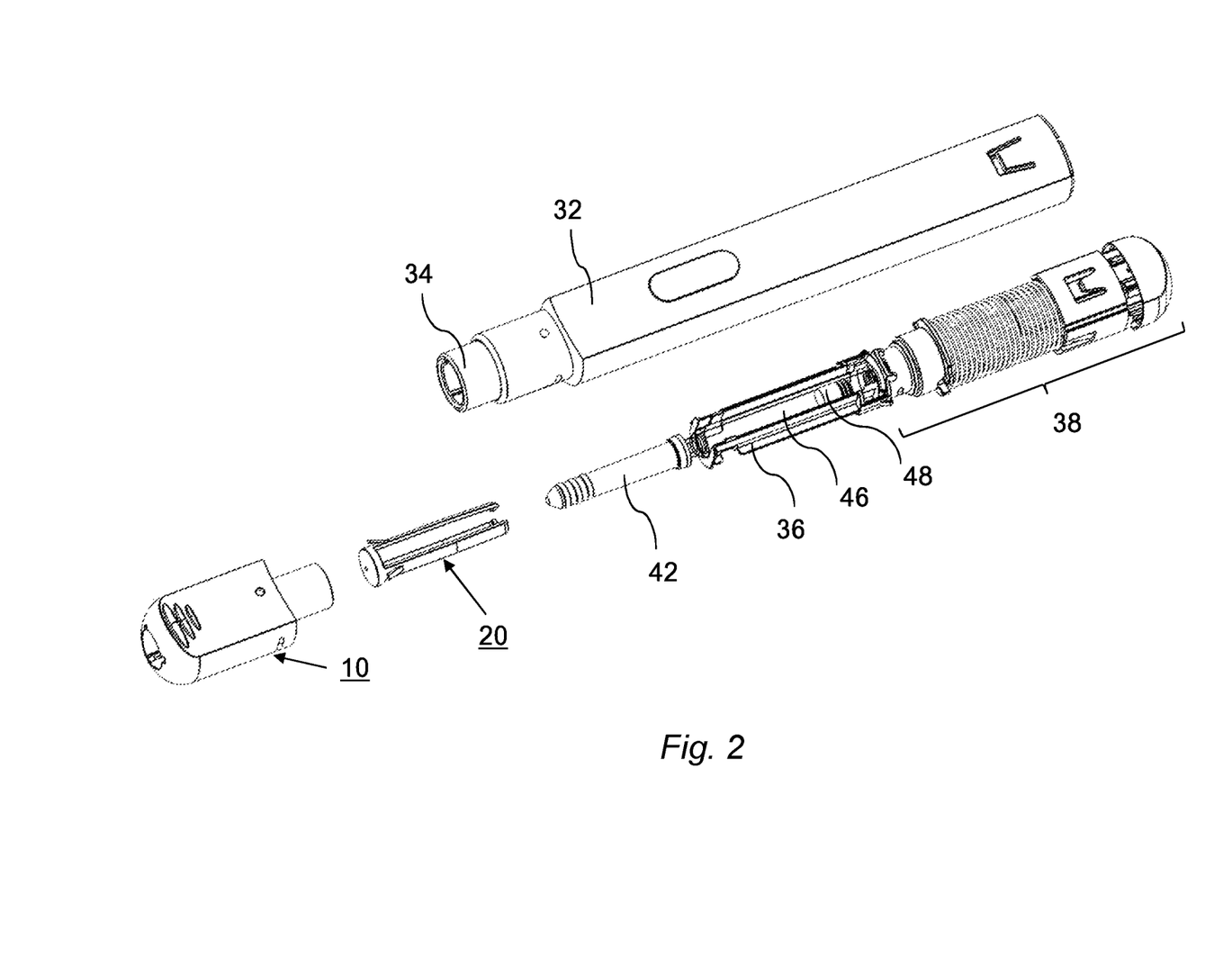
FIG. 2 is an exploded perspective view of an exemplary embodiment of the device shown in FIG. 1.

FIG. 2 illustrates an exploded perspective view of the embodiment of FIG. 1. The delivery device is shown to comprise a housing 32, an extendable needle guard 34, a container holder 36 and a power pack 38. A medicament container 46, containing a medicament and a stopper 48, may be accommodated in the container holder 36. A needle (not shown) is attached to a proximal end of the medicament container 46. The needle is in turn covered by a needle sheath 42. The needle sheath is preferably made of a soft and resiliently flexible material, e.g. rubber.

Also illustrated in FIG. 2 is the sheath remover assembly, comprising the cap 10 and the sheath grabber 20. In FIG. 2 the cap and grabber are shown in an unassembled state. When the device is delivered to a user, the cap and grabber are assembled and attached to the proximal end of the housing 32, as shown in FIG. 1, such that the cap and the sheath grabber may interact to engage and to remove the needle sheath 42 from the needle when the user removes the cap from the delivery device by pulling it proximally in relation to the housing, as will be explained below.

Figure 3:
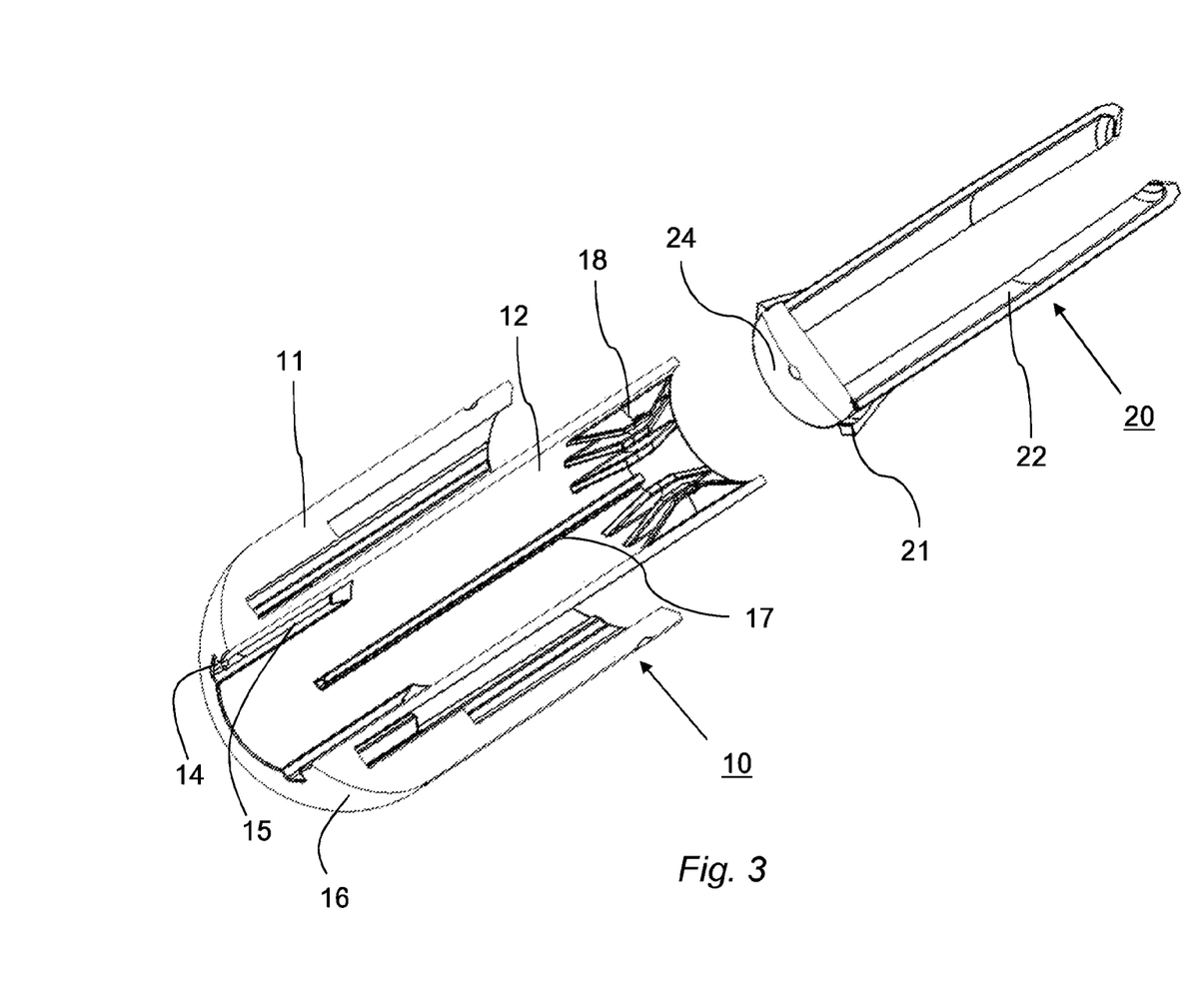
FIG. 3 is an exploded cross-section of an exemplary embodiment of the present invention.

FIG. 3 shows a detailed view of an exploded cross-section of the sheath remover assembly. The cap 10 comprises an outer tubular member 11 and an inner coaxial tubular member 12, which are integrally arranged, or joined together, by a generally annular transversal wall 16, extending between the proximal ends of the inner and outer tubular members. Thus, the proximal end of the inner tubular member 12 is open, such that it may receive the sheath grabber 20 upon assembly of the cap and the sheath grabber. In FIG. 3, the annular transversal wall is substantially dome-shaped, but could also be of any other shape without affecting the functionality of the current invention. When assembled, the sheath grabber 20 is coaxially and slidably arranged within the inner tubular member 12 of the cap.

In the exemplary embodiment, the inner circumferential surface of the inner tubular member 12 of the cap further comprises first blocking means 14, second blocking means 17 and biasing means 18, which are configured to interact with first stop means 21, second stop means 24 and engaging means 22, respectively, comprised by the sheath grabber.

The first stop means 21 of the sheath grabber, in the exemplary embodiment of FIG. 3, is in the form of latch members integral with, or attached to, a proximal part of the engaging means 22, such that said latch members are resiliently flexible in a radial direction but substantially rigid in a longitudinal direction. In the assembled device the first stop means 21 is slidably arranged to a guide means 15 and configured to interact with the first blocking means 14 for holding the sheath grabber 20 within the cap 10.

The second stop means 24 of the sheath grabber is a transversal member and may be configured in the shape of a transversal wall part configured such that said transversal wall part may be accommodated inside the inner tubular member 12 of the cap 10. The engaging means 22 extend distally from a distal surface of said transversal wall part.

The engaging means 22 may, for instance, comprise at least two radially resilient flexible arms extending longitudinally from the transversal member, equally spaced along a peripheral edge of the distal surface of said first stop means 21 and configured to be resiliently flexible in a radial direction. The first stop means 21 may be flexible latch members integral with, or attached to, the at least two radially resilient flexible arms. A distal part of the engaging means 22 is arranged with gripping structures for improved friction between the engaging means and the needle sheath 42 during a sheath removal operation. For instance, each of the at least two radially resilient flexible arms may comprise hooks or radially inwardly directed edges, grooves and/or protrusions for improving friction and/or connection between the engaging means and the needle sheath 42.

The first blocking means 14 is arranged at a proximal end of a guide means 15. The first blocking means may be in the form of a distally directed surface, e.g. a ledge, arranged inside or integrally within the guide means. The guide means may be configured as at least two longitudinal grooves extending distally from the proximal end of the of the inner circumferential surface of the inner tubular member 12 such that the first stop means 21, e.g. the latch members, may be slidably arranged within said grooves. It would also be possible to use ridges or ribs instead of grooves. In such a case it would obviously be necessary to also modify the latch members, the first blocking means and the second stop means to be able to interact with a ridge instead of a groove, but such modifications are well within the capability of a skilled person.

When the cap and the sheath grabber are positioned in relation to each other such that a proximally directed surface of the first stop means 21 of the sheath grabber abuts the distally directed surface of the first blocking means 14 of the cap, the sheath remover assembly is defined to be in a first state.

The second blocking means 17 is also arranged on the inner circumferential surface of the inner tubular member 12, for instance in the shape of at least two longitudinally extending ribs. A proximal end of the second blocking means is configured with a proximally directed ledge at a predetermined distance from the proximal end of the inner tubular member. When the cap and the sheath grabber are positioned in relation to each other such that a distally directed surface of the second stop means 24 of the sheath grabber abuts the proximally directed ledge of the second blocking means 17 of the cap, the sheath remover assembly is defined to be in a second state.

The cap is coaxially movable relative to the sheath grabber preferably wherein movement of the sheath grabber is restricted by the interaction between the biasing means 18 and the engaging means 22 such that the grabber is biased to engage the sheath 42 and wherein movement of the cap relative to the sheath grabber is restricted by the interaction between the second blocking means 17 and the second stop means 24 such that the cap, the grabber and the sheath can be removed from the device The second stop means 24 is positioned at a predetermined distance from the second blocking (17) means when the cap is attached to the device such that the second stop means and the second blocking means abut each other when the cap is coaxially moved in relation to the grabber said predetermined distance such that the cap biases the sheath grabber to move axially.

The distal part of the inner tubular member 12 is arranged with biasing means 18. In the exemplary embodiment of FIG. 3 the biasing means is configured as a number of radially protruding, longitudinally elongated fins, equally spaced along the inner circumferential surface of the inner tubular member. The fins are ramp-shaped, such that the sloping edges of the fins slope from the inner surface of the inner tubular member in a direction towards the distal end of said inner tubular member, up to a predetermined height at a predetermined distance from the distal end of the inner tubular member. Said height and distance are adapted to the configuration of the engaging means 22 for biasing said engaging means radially inwards and thereby achieve a maximum engaging force between the engaging means and the needle sheath 42 when the cap is coaxially movable relative to the sheath grabber. The angle between the sloping edges of the fins and the inner surface of the inner tubular member is preferably less than 45 degrees.

The function of the shield remover assembly will now be described in conjunction with FIG. 4A and 4B. After manufacturing, the component parts of the device are assembled. For the sheath remover assembly, this means inserting the sheath grabber 20 into the inner tubular member 12 of the cap 10. The sheath grabber is aligned with the cap such that the first stop means 21 enter the guide means 15 by pushing the sheath grabber distally in relation to the cap until the first stop means snap past the first blocking means 14. The cap and the sheath remover are then mechanically connected and axially movable in relation to each other between the first state and the second state as described above. The cap and the sheath remover are rotationally locked about the axis in relation to each other since the first stop means 21 protrudes into the groove of the guide means 15. In the first state the proximal surface of the second stop means 24 may be flush with the proximal surface of the cap as shown in FIG. 1.

When a medicament container 46 with a needle 44 and a needle sheath 42 has been loaded into the delivery device 30 the sheath remover assembly may be mounted on the delivery device such that the sheath remover assembly covers the needle sheath. During mounting, as the assembly is pushed distally in relation to the delivery device and the sheath, the engaging means 22 is forced slightly radially outwards by the needle sheath such that a slight pressure, i.e. friction or connection, is achieved between the engaging means and the needle sheath 42. During this movement the first stop means 21 abuts the first blocking means 14. At the end of the mounting movement a distal part of the outer tubular member 11 engages a proximal part of the housing 32 such that a mechanical connection is established between the sheath remover assembly and the housing. In the exemplary embodiment the connection is frictional and may be broken by simply pulling the cap and the housing apart, but other forms of connections are conceivable, e.g. a threaded connection or a bayonet coupling. It is important to note that, in the first state, a turning movement of the sheath remover assembly about the axis would not turn the sheath since the grabber is not squeezing the sheath.

Figure 4A:
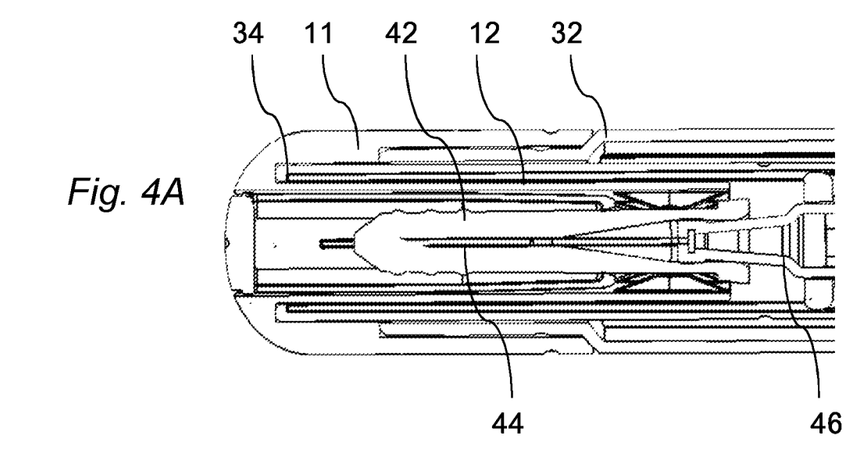
FIG. 4A & 4B are cross-sections showing the working principle of the present invention.
Figure 4B:
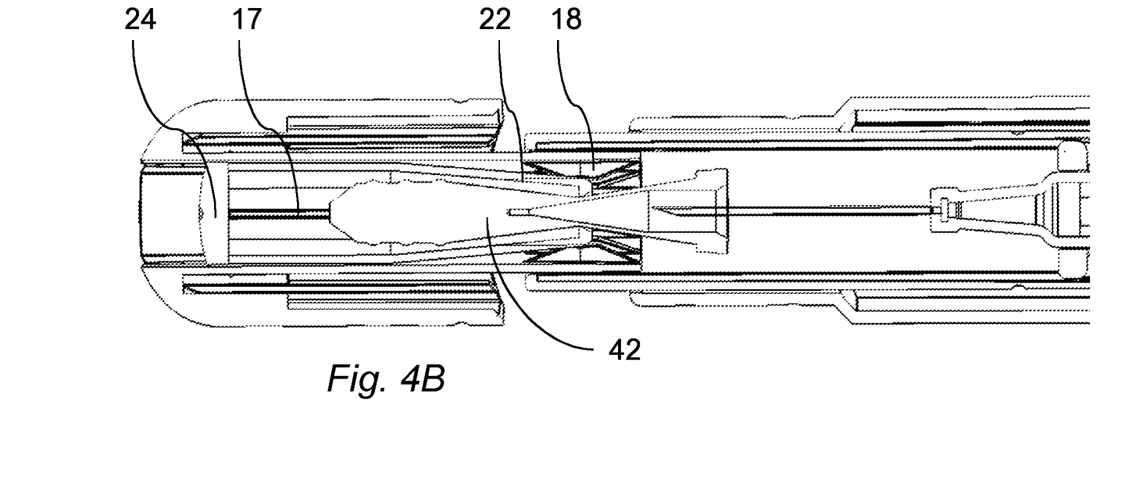

The medicament delivery device is thus delivered to the user with the sheath remover assembly mounted to the device in the first state as shown in FIG. 1 and FIG. 4A.

In order to prepare the device for administration of medicament the user has to remove the needle sheath 42 from the needle 44. This is accomplished by the user pulling at the cap 10 proximally in relation to the housing 32. As the frictional force between the cap and the housing is overcome the cap starts to move proximally relative to the housing.

Initially, due to the slight friction/connection between the engaging means 22 and the needle sheath 42, the sheath grabber 20 is not displaced axially by the cap, but remains stationary relative to the housing. When the biasing means 18 of the cap makes contact with the engaging means of the grabber, interaction between the biasing means and the engaging means therefore wedges the engaging means between the biasing means and the needle sheath and forces the flexible engaging means radially inwards, increasing the radial pressure on the needle sheath for engaging it. In the exemplary embodiment, this is illustrated by the arms of the engaging means climbing up the ramps of the biasing means, while at the same time the gripping structures of the engaging means dig into the relatively soft rubber material of the needle sheath.

As the sheath remover assembly reaches the second state the second stop means 24 is brought into abutment with the second blocking means 17. At this point the engaging means has reached a maximum engagement with the needle sheath. This is exemplified by the gripping structures of the engaging means in FIG. 4B being aligned with the predetermined maximum height of the fins. Since the second stop means and the second blocking means abut each other the cap and the sheath grabber are now stationary in relation to each other.

Hypothetically, if the biasing means was allowed to pass the gripping structures of the exemplary embodiment the arms of the engaging means would risk flexing radially outwards again, thereby decreasing the grip on the needle sheath. Therefore the maximum height of the biasing means is arranged at a predetermined distance from the proximal end of the second blocking means 17 equal to the longitudinal length of the engaging means, such that the exemplary gripping structures come to rest at a maximum engagement with the needle sheath in the second state of the sheath remover assembly.

Accordingly, as the user continues to pull at the cap, interaction between the second stop means and the second blocking means forces the sheath remover assembly to continue movement as a unit, i.e. the sheath grabber starts to move together with the cap relative to the delivery device. Since the engagement between the sheath grabber and the needle sheath is strong at this point, the needle sheath is forced to move along together with the sheath remover assembly. As the needle sheath is removed from the needle, the device is ready for administration of medicament.

In other words, the cap is coaxially movable relative to the sheath grabber in a proximal direction, whereas the movement of the sheath grabber is restricted by the interaction between the biasing means and the engaging means such that the grabber is biased to engage the sheath and movement of the cap relative to the sheath grabber is restricted by the interaction between the second blocking means and the second stop means such that the cap, the grabber and the sheath can be removed from the device when pulled in a proximal direction.

The second stop means is positioned at a predetermined distance from the second blocking means when the cap is attached to the device so that the second stop means and the second blocking means abut each other when the cap is coaxially moved proximally in relation to the grabber said predetermined distance such that the cap biases the sheath grabber to move axially in the proximal direction. While the invention has been illustrated and described in detail in the drawings and foregoing description, such illustration and description are to be considered illustrative or exemplary and not restrictive. It will be understood that changes and modifications may be made by those of ordinary skill within the scope of the following claims. In particular, the present invention covers further embodiments with any combination of features from different embodiments described above and below.

Furthermore, in the claims the word "comprising" does not exclude other elements or steps, and the indefinite article "a" or "an" does not exclude a plurality. A single unit may fulfil the functions of several features recited in the claims. The terms "essentially", "about", "approximately" and the like in connection with an attribute or a value particularly also define exactly the attribute or exactly the value, respectively. Any reference signs in the claims should not be construed as limiting the scope.

The invention claimed is:

1. A needle sheath remover assembly for a medicament delivery device, axially elongated in a proximal and a distal direction, comprising:
   a cap configured for removable attachment to a housing of the medicament delivery device, the cap comprising a second blocking device and a biasing device;
   a sheath grabber connected to the cap and configured for engaging a needle sheath of a medicament container in the medicament delivery device, the sheath grabber comprising a second stop device and an engaging device;
   wherein the cap and sheath grabber are axially movable in relation to each other and are configured for interaction with each other such that upon removal of the cap from the housing, the sheath grabber is able to engage and remove the needle sheath; movement of the sheath grabber is restricted by interaction between the biasing device and the engaging device such that the sheath grabber is biassed to engage the needle sheath; and movement of the cap relative to the sheath grabber is restricted by interaction between the second blocking device and the second stop device such that the cap, the sheath grabber, and the needle sheath are removable from the medicament delivery device.

2. The needle sheath remover assembly of claim 1, wherein the cap comprises an outer tubular member and an inner coaxial tubular member.

3. The needle sheath remover assembly of claim 2, wherein the second blocking device includes at least two longitudinally extending ribs on an inner circumferential surface of the inner coaxial tubular member.

4. The needle sheath remover assembly of claim 2, wherein the biasing device includes a number of radially protruding, longitudinally elongated fins equally spaced around an inner circumferential surface of the inner coaxial tubular member, and the fins are ramp-shaped such that edges of the fins slope from the inner circumferential surface toward a distal end of the inner coaxial tubular member.

5. The needle sheath remover assembly of claim 4, wherein the fins protrude up to a predetermined height at a predetermined distance from the distal end of the inner coaxial tubular member, and the height and distance are adapted to the engaging device for biasing the engaging device radially inward and enhancing an engaging force between the engaging device and the needle sheath when the cap is coaxially moved relative to the sheath grabber.

6. The needle sheath remover assembly of claim 2, wherein the sheath grabber is coaxially and slidably arranged within the inner coaxial tubular member.

7. The needle sheath remover assembly of claim 1, wherein the second stop device is at a predetermined distance from the second blocking device when the cap is attached to the medicament delivery device, and the second stop device and the second blocking device abut each other when the cap is coaxially moved in relation to the sheath grabber the predetermined distance such that the cap biases the sheath grabber to move axially.

8. A needle sheath remover assembly for a medicament delivery device, axially elongated in a proximal and a distal direction, comprising:
   a cap configured for removable attachment to a housing of the medicament delivery device, the cap comprising a second blocking device and a biasing device;
   a sheath grabber connected to the cap and configured for engaging a needle sheath of a medicament container in the medicament delivery device, the sheath grabber comprising a second stop device and an engaging device;
   wherein the cap and sheath grabber are axially movable in relation to each other and are configured for interaction with each other such that upon removal of the cap from the housing, the sheath grabber is able to engage and remove the needle sheath; movement of the sheath grabber is restricted by interaction between the biasing device and the engaging device such that the sheath grabber is biassed to engage the needle sheath; movement of the cap relative to the sheath grabber is restricted by interaction between the second blocking device and the second stop device such that the cap, the sheath grabber, and the needle sheath are removable from the medicament delivery device; the cap comprises an outer tubular member and an inner coaxial tubular member; and the outer tubular member and the inner tubular member are integral or joined together by a generally annular transversal wall that extends between proximal ends of the inner and outer tubular members.

9. A needle sheath remover assembly for a medicament delivery device, axially elongated in a proximal and a distal direction, comprising:
   a cap configured for removable attachment to a housing of the medicament delivery device, the cap comprising a second blocking device and a biasing device;
   a sheath grabber connected to the cap and configured for engaging a needle sheath of a medicament container in the medicament delivery device, the sheath grabber comprising a second stop device and an engaging device;
   wherein the cap and sheath grabber are axially movable in relation to each other and are configured for interaction with each other such that upon removal of the cap from the housing, the sheath grabber is able to engage and remove the needle sheath; movement of the sheath grabber is restricted by interaction between the biasing device and the engaging device such that the sheath grabber is biassed to engage the needle sheath; movement of the cap relative to the sheath grabber is restricted by interaction between the second blocking device and the second stop device such that the cap, the sheath grabber, and the needle sheath are removable from the medicament delivery device; the cap comprises an outer tubular member and an inner coaxial tubular member; the sheath grabber is coaxially and slidably arranged within the inner coaxial tubular member; and the sheath grabber further comprises a first stop device, and the cap further comprises a guide and a first blocking device arranged to the guide.

10. The needle sheath remover assembly of claim 9, wherein the first stop device is slidably arranged to the guide and is configured for interaction with the first blocking device for holding the sheath grabber in the cap.

11. The needle sheath remover assembly of claim 9, wherein the second stop device includes a transversal member, the engaging device comprises at least two radially resilient flexible arms extending longitudinally from the transversal member, and the first stop device includes flexible latch members integral with or attached to the at least two radially resilient flexible arms.

12. The needle sheath remover assembly of claim 11, wherein the at least two radially resilient flexible arms comprise hooks or radially inwardly directed edges, grooves, or protrusions for enhancing connection between the engaging device and the needle sheath.

13. The needle sheath remover assembly of claim 9, wherein the guide includes at least two longitudinally extending grooves or ridges on an inner circumferential surface of the inner coaxial tubular member, and the first blocking device includes a distally directed surface or ledge that is integral or arranged inside each of the at least two longitudinally extending grooves or ridges.

\* \* \* \* \*